US00PP33263P2

(12) United States Plant Patent
Van Swieten

(10) Patent No.: US PP33,263 P2
(45) Date of Patent: Jul. 13, 2021

(54) *PHALAENOPSIS* ORCHID PLANT NAMED 'PHALHALLY'

(50) Latin Name: ***Phalaenopsis* hybrid**
Varietal Denomination: PHALHALLY

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/300,004

(22) Filed: Feb. 3, 2021

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — Jondle & Associates, P.C.

(57) ABSTRACT

A new and distinct variety of *Phalaenopsis* plant named 'PHALHALLY', particularly characterized by purplish-red, striped flowers with dark red-purple lips, a flat flower shape in lateral view, a concave lateral sepal shape in cross section, and is propagated by meristem tissue culture, is disclosed.

3 Drawing Sheets

Genus and species: *Phalaenopsis* hybrid.
Variety denomination: 'PHALHALLY'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALHALLY'.

The new *Phalaenopsis* plant is a product of a planned breeding program conducted by the inventor in Bleiswijk, the Netherlands. The objective of this breeding program was to create a new *Phalaenopsis* plant with purplish-red, striped flowers and dark red-purple lips, suitable for potted plant production.

The new *Phalaenopsis* plant 'PHALHALLY' is a result of cross-pollination made by the inventor in November 2010 in Bleiswijk, the Netherlands, of the proprietary female, or seed parent, *Phalaenopsis* hybrid '01-1434' (unpatented) with the proprietary male, or pollen parent, *Phalaenopsis* hybrid '01-3705' (unpatented).

The new *Phalaenopsis* was selected by the inventor as a single plant within the progeny of the stated cross-pollination in a controlled greenhouse in Bleiswijk, the Netherlands, in September 2013. Asexual reproduction of the new *Phalaenopsis* plant by meristem tissue culture since 2015 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Aug. 30, 2019 (Application no. 2019/2068), by Applicant who obtained the subject matter disclosed directly from the inventor. 'PHALHALLY' has not been made publicly available or sold anywhere in the world prior to the effective filing date of this application with the exception of sales or disclosures made one year or less before the effective filing date of this claimed invention by Applicant who obtained 'PHALHALLY' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALHALLY' as a new and distinct variety of *Phalaenopsis* plant:

1) Purplish-red, striped flowers with dark red-purple lips (after opening, reddish color of the flower fades and it becomes more purple);
2) Flower shape in lateral view is flat; and
3) Lateral sepal shape in cross section is concave.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in December 2020. Colors in the photographs may differ from the color values cited in the detailed botanical description, which accurately describe the actual colors of the new variety.

DESCRIPTION OF THE NEW VARIETY

Figure 1:
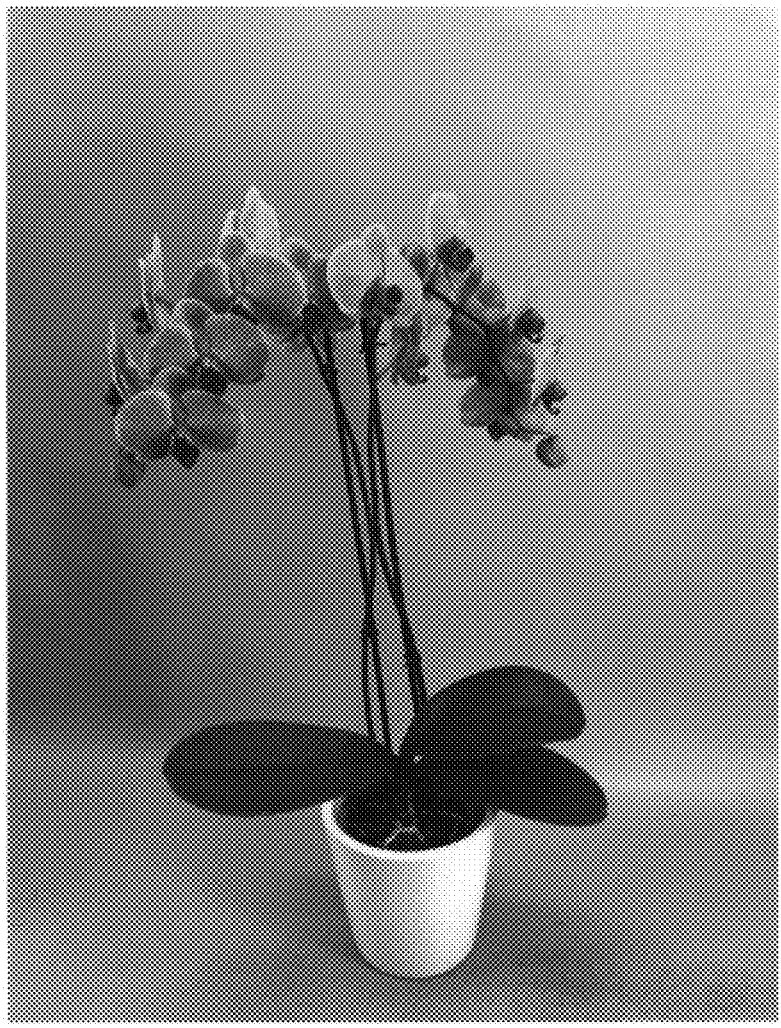
FIG. 1 shows the overall plant habit, including blooms, buds, and foliage of 'PHALHALLY'.
Figure 2:
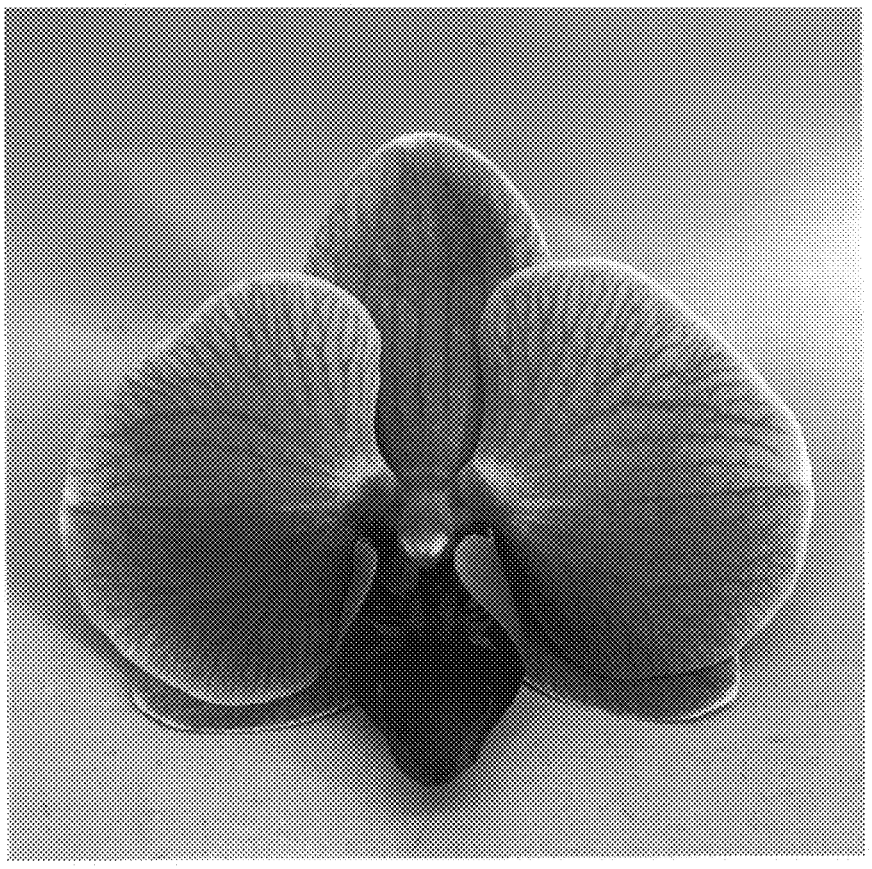
FIG. 2 shows a close-up of a flower of 'PHALHALLY'.
Figure 3:
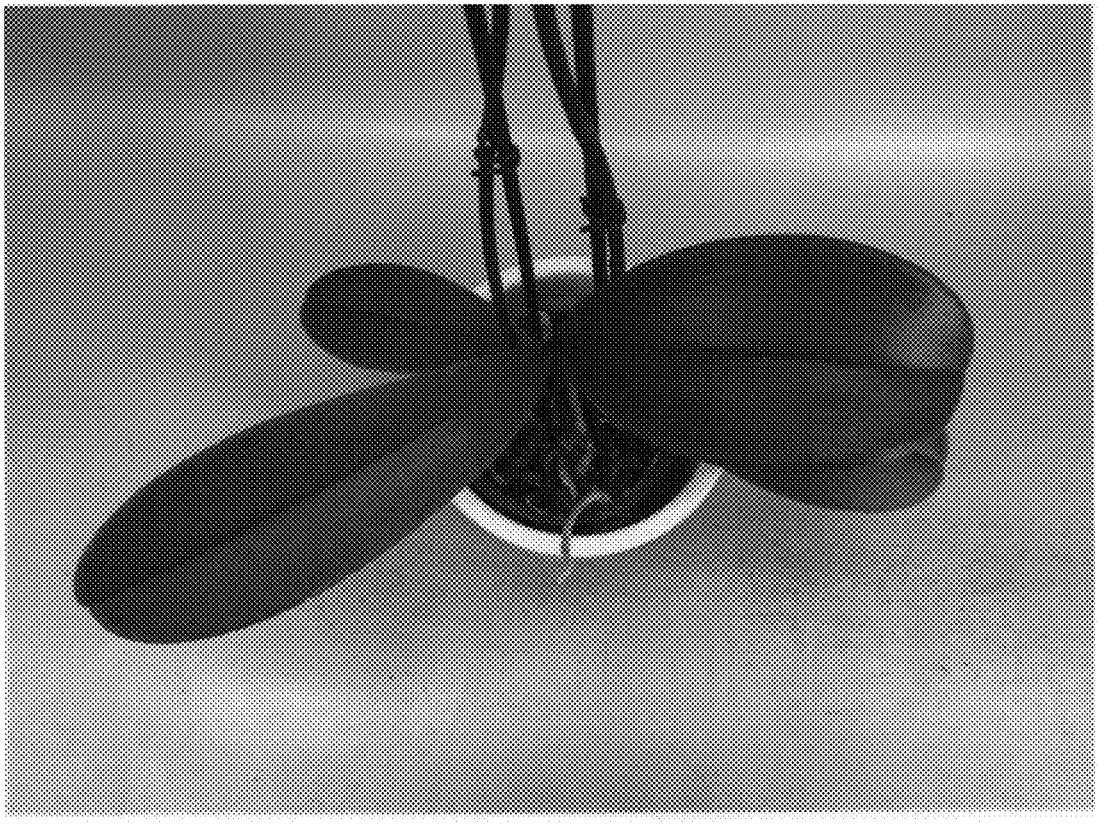
FIG. 3 shows an overhead view of the leaves of 'PHALHALLY'.

The following detailed description sets forth the distinctive characteristics of 'PHALHALLY'. Plants of the new

*Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in December 2020 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALHALLY'.

Parentage:

*Female parent*.—*Phalaenopsis* cultivar '01-1434' (unpatented).

*Male parent*.—*Phalaenopsis* cultivar '01-3705' (unpatented).

Propagation:

*Type*.—Meristem tissue culture.

Roots:

*Root description*.—Greyed-green (something between RHS 190B and 190C) colored roots with branching lateral roots having yellow-green (RHS 144C) with a hint of purplish-red (RHS N77B) colored root tips.

Plant:

*Crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with raceme inflorescence.

*Height* (*from soil level to top of inflorescence*).—Approximately 50.0 cm to 55.0 cm.

*Width* (*measured from leaf tips*).—About 23.0 cm to 26.0 cm.

*Vigor*.—Strong.

Leaves:

*Mature leaves*.—Quantity per plant: 7 to 8 leaves are produced before flowering. Length (fully expanded): 15.0 cm to 18.0 cm. Width: 6.5 cm to 7.5 cm. Position of broadest part of the leaf: Toward apex. Shape: Obovate. Base shape: Moderately elongated. Apex: Unequal obtuse. Leaf blade angle with the petiole (measured from the horizontal position): Between 10 degrees and 25 degrees. Leaf margin: Entire. Color: Upper surface: RHS 147A. Lower surface: RHS 147B and diluting dark red (RHS 187A) toward margin and tip. Texture (both upper and lower surfaces): Smooth. Thickness: 2.0 mm to 3.0 mm. Variegation: Absent. Venation: Pattern: Parallel. Color of the midvein: Upper surface: RHS 147A. Lower surface: RHS 146A and diluting dark red (RHS 187A) toward the tip.

Peduncle:

*Quantity per plant*.—1 to 2.

*Number of flowers per peduncle*.—7 to 10.

*Length*.—50.0 cm to 55.0 cm.

*Diameter*.—4.0 mm to 5.0 mm.

*Strength*.—Strong.

*Aspect*.—Upright to slightly pendent.

*Texture*.—Smooth.

*Color*.—Reddish-brown (RHS 200A).

*Internode length*.—3.5 cm to 4.5 cm.

Inflorescence description:

*Appearance*.—Upright to slightly pendent, raceme inflorescence with bilaterally symmetrical flowers that open in succession beginning with the lowermost flower.

*Number of inflorescences*.—1 to 2.

*Inflorescence size*.—Height (from base to tip): 140.0 mm to 190.0 mm.

*Flowering time*.—First flowers can be expected 10 to 11 months after planting in a 12-cm pot.

*Flower*.—Height: 73.0 mm to 78.0 mm. Diameter: 85.0 mm to 90.0 mm. Depth of lip: 25.0 mm to 27.0 mm.

*Flower longevity*.—On the plant: 8 to 10 weeks.

*Flower shape*.—Flat.

*Fragrance*.—Absent.

*Flower bud*.—Average size: Medium to large. Length: 22.0 mm to 24.0 mm. Width: 18.0 mm to 20.0 mm. Shape: Egg shaped. Color: Yellow-green (something in between RHS 146D and 152D) at the base and purplish-red (something in between RHS N77B and 187B) toward the tip.

*Petals*.—Arrangement: Open/free. Shape: Semi-circular. Apex: Rounded asymmetric. Margin: Weakly undulated. Length (from base to tip): 41.0 mm to 43.0 mm. Width: 51.0 mm to 53.0 mm. Position of the broadest part of the petal: Toward the base. Color (when fully opened): Upper surface: Basic color: Light greenish-yellow (RHS 160C). Over color: Touch of very purplish-red (RHS 72A) and light purple (RHS 75B) at the base; purplish-red shade (RHS 185C) and purplish-red stripes (RHS 70A). Lower surface: Basic color: Light yellow (something in between RHS 160B and 160C). Over color: Purplish-pink (RHS 186D) at the base; purplish-pink shade (RHS 186C) and diluting purplish-pink stripes (something in between RHS 186B and 186C). Number of spots and stripes on the petals (upper surface): Many stripes. Color of spots and stripes on the petals (upper surface): RHS 70A. Density of netting of the petals (upper surface): None. Color of the netting (upper surface): Not applicable.

*Dorsal sepal*.—Shape: Elliptic. Apex: Obtuse to rounded symmetric. Margin: Entire. Length (from base to tip): 43.0 mm to 45.0 mm. Width: 33.0 mm to 35.0 mm. Position of the broadest part of the dorsal sepal: At the middle. Color (when fully opened): Upper surface: Basic color: Yellow-green (something in between RHS 160B and 160C). Over color: Hint of purplish-red (RHS 70A) at the base; stripes (RHS 186A); purplish-red shade (RHS 185C) and toward the tip (RHS 186B). Lower surface: Basic color: Yellow-green (something in between RHS 153A and 160C). Over color: Touch of diluting purplish-red (RHS 186B) at the base and dark pink (RHS 182D) toward margins; diluting stripes (RHS 186B). Number of spots and stripes on the dorsal sepals (upper surface): Many stripes. Color of spots and stripes on the dorsal sepals (upper surface): RHS 186A. Density of netting of the dorsal sepals (upper surface): Low to medium. Color of the netting: RHS 186A.

*Lateral sepals*.—Shape: Ovate. Apex: Obtuse symmetric. Margin: Entire. Length (from base to tip): 40.0 mm to 42.0 mm. Width: 28.0 mm to 30.0 mm. Position of the broadest part of the lateral sepal: At the base. Color (when fully opened): Upper surface: Basic color: Light yellow (RHS 160B). Over color: Dark purplish-red stripes (RHS N79C); red-purple shade (something in between RHS 184B and 184C). Lower surface: Basic color: Yellow-green (something in between RHS 153A and 160C). Over color: Purplish shade (RHS 185C) toward margin, from base toward tip; stripes (RHS 186A). Number of spots, dots, and stripes on the lateral sepals (upper surface): Medium stripes and medium dots at the base. Color of spots, dots, and stripes on the lateral sepals (upper surface): Stripes (RHS N79C); dots (RHS 183B). Density of netting of the lateral sepals (upper surface): Low to medium. Color of the netting (upper surface): RHS 186A.

*Labellum* (*lip*).—Whiskers: Present. Length of whiskers: 9.0 mm to 11.0 mm. Color of whiskers: Dark red (RHS 59A). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Entire. Length: 19.0 mm to 21.0 mm. Width: 14.0 mm to 16.0 mm. Color: Upper surface: Touch of yellow (RHS 8A) and dark red stripes (RHS 59A) at the base; dark red (RHS 59A) and purplish-red (something in between RHS 70A and 70B) toward the tip. Lower surface: Touch of greenish-white (RHS 157A) at the base; dark red (RHS 13B) toward margin on one side and purplish-red (something in between RHS 70A and 70B) toward the tip. Number of spots and stripes on the lateral lobe: Few stripes. Color of spots and stripes on the lateral lobe: RHS 59A. Density of netting of the lateral lobe: None. Color of the netting: Not applicable.

*Apical lobe*.—Shape: Triangular to trullate. Margin: Entire. Length: 17.0 mm to 19.0 mm. Width: 19.0 mm to 21.0 mm. Color: Upper surface: Dark red (RHS 59A) at the base and purplish-red (RHS 59B) toward whiskers. Lower surface: Dark purplish-red toward wings (from RHS 59B to 59A at wings); hint of light yellow-green (RHS 157A) at the middle from the base toward whiskers; dark purplish-red (RHS N79C) toward whiskers. Number of spots and stripes on the apical lobe: None. Color of spots and stripes on the apical lobe: Not applicable. Density of netting of the apical lobe: None. Color of the netting: Not applicable.

*Callus*.—Average size: Small to medium. Height: 6.0 mm to 7.0 mm. Length: 4.0 mm to 5.0 mm. Width: 3.0 mm to 4.0 mm. Color: Yellow tips (RHS 9A); lighter yellow (RHS 9C) on sides; dotted (RHS 187B).

Reproductive organs:

*Column*.—Length: 8.0 mm to 10.0 mm. Diameter: 5.0 mm to 6.0 mm. Color: Reddish-purple (RHS N78B).

*Pollinia*.—Quantity: 2. Diameter: 0.9 mm to 1.1 mm. Color: Orange-yellow (RHS 23A).

*Ovary*.—Length: 12.0 mm to 14.0 mm. Diameter: 1.9 mm to 2.2 mm.

*Pedicel*.—Length: 37.0 mm to 39.0 mm. Diameter: 2.3 mm to 2.6 mm. Texture: Smooth. Color: Hint of dark purplish-red (RHS N79B) at the base; yellow-green (something in between RHS 145B and 145C) and reddish-purple (RHS N78B) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALHALLY' differs from the female parent plant '01-1434' (unpatented) in that 'PHALHALLY' has larger flowers than '01-1434'.

'PHALHALLY' differs from the male parent plant '01-3705' (unpatented) in that 'PHALHALLY' has a medium curvature of the lateral lobe, whereas '01-3705' has a weak curvature of the lateral lobe. Additionally, 'PHALHALLY' has larger flowers than '01-3705'.

'PHALHALLY' is most similar to the commercial *Phalaenopsis* plants named 'PHALVILMYK' (U.S. Plant Pat. No. 32,008) and 'PHALIFQUDI' (U.S. Plant Pat. No. 26,831). 'PHALHALLY' differs from the commercial variety 'PHALVILMYK' in that 'PHALHALLY' has spatulate lateral lobes, whereas 'PHALVILMYK' has weakly spatulate lateral lobes. Additionally, 'PHALHALLY' has larger flowers and longer whiskers than 'PHALVILMYK'.

'PHALHALLY' differs from the commercial variety 'PHALIFQUDI' in that 'PHALHALLY' has larger flowers, shorter whiskers, and narrower leaves than 'PHALIFQUDI'.

I claim:

1. A new and distinct variety of *Phalaenopsis* plant named 'PHALHALLY', substantially as described and illustrated herein.

* * * * *